(12) United States Patent
Todd (10) Patent No.: US 9,307,930 B2
(45) Date of Patent: Apr. 12, 2016

(54) PATIENT INTERFACE SIZING GAUGE

(71) Applicant: KONINKLIJKE PHILIPS N.V., Eindhoven (NL)

(72) Inventor: Jonathan Paul Todd, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 70 days.

(21) Appl. No.: 14/376,144

(22) PCT Filed: Jan. 31, 2013

(86) PCT No.: PCT/IB2013/050824
§ 371 (c)(1),
(2) Date: Aug. 1, 2014

(87) PCT Pub. No.: WO2013/118034
PCT Pub. Date: Aug. 15, 2013

(65) Prior Publication Data
US 2015/0007439 A1   Jan. 8, 2015

Related U.S. Application Data

(60) Provisional application No. 61/595,193, filed on Feb. 6, 2012.

(51) Int. Cl.
*A61B 5/107* (2006.01)
*A61M 16/06* (2006.01)
*G01B 3/38* (2006.01)

(52) U.S. Cl.
CPC .............. *A61B 5/1075* (2013.01); *A61M 16/06* (2013.01); *A61M 16/0605* (2014.02); *G01B 3/38* (2013.01); *A61M 2016/0661* (2013.01)

(58) Field of Classification Search
CPC . A61B 5/107; A61B 5/1075; A61M 16/0605; G01B 3/38
USPC .................................................... 33/512, 515
See application file for complete search history.

(56) References Cited

U.S. PATENT DOCUMENTS 1,804,567 A * 5/1931 Pray ........................ A61C 19/04
33/513
2,048,989 A * 7/1936 Baribeau ................ A61B 5/107
33/513

(Continued)

OTHER PUBLICATIONS

Anonymous: "FlexiFit 432 CPAP Mask Sizing Guide", Fisher & Paykel, Jan. 1, 2012, XP002698827, Retrieved from the Internet: URL:http://web.archi ve.org/1i veweb/http://www.cpapxchange.com/cpap-masks-bipap-masks/flexifit-infinity-cpap-sizing-guide.pdf.

(Continued)

*Primary Examiner* — Yaritza Guadalupe-McCall
(74) *Attorney, Agent, or Firm* — Michael W. Haas (57) ABSTRACT

A sizing gauge (4) is structured to be used with a patient (8) and is structured to enable an identification of a particular patient interface that is most appropriately sized for the patient. The sizing gauge includes a support portion (12) and a sizing portion (16). The sizing portion includes a first gauge element (36) and a plurality of second gauge elements (40A, 40B,40C). The first gauge element is disposed on the support portion and is structured to be positioned at a first location on the patient's face. The plurality of second gauge elements are disposed on the support portion and are situated at locations spaced from the first gauge element. The distance between the first gauge element and each second gauge element is representative of a size in one direction (44) of each of at least some of the plurality of patient interfaces. At least one of the plurality of second gauge elements comprises a tactile feature.

13 Claims, 6 Drawing Sheets

(56) References Cited

U.S. PATENT DOCUMENTS

| | | | | |
|---|---|---|---|---|
| 2,107,534 | A * | 2/1938 | Houser | A61B 5/107 33/513 |
| 2,566,903 | A * | 9/1951 | Moran | A61C 19/045 33/513 |
| 3,300,864 | A * | 1/1967 | Lesslie | A61B 5/107 33/512 |
| 4,843,720 | A * | 7/1989 | Kim | A61B 5/107 33/512 |
| 5,170,570 | A * | 12/1992 | Mays, Jr. | A41D 19/046 33/2 R |
| 5,235,988 | A * | 8/1993 | Johnson | A61B 5/1077 33/512 |
| 5,576,778 | A * | 11/1996 | Fujie | G06T 11/203 33/200 |
| 5,584,125 | A * | 12/1996 | Prete | G01B 3/38 33/512 |
| 5,685,084 | A * | 11/1997 | Demers | A61C 19/04 33/513 |
| 5,927,973 | A * | 7/1999 | Hanebaum | A61C 19/04 33/513 |
| 6,160,264 | A * | 12/2000 | Rebiere | A43D 1/02 33/515 |
| 7,699,607 | B2 * | 4/2010 | Margossian | A61C 19/045 33/511 |
| 7,895,765 | B2 * | 3/2011 | Plain | A45D 40/30 33/512 |
| D650,905 | S | 12/2011 | Plascott | |
| 8,254,637 | B2 * | 8/2012 | Abourizk | A61M 16/06 356/601 |
| 2006/0235877 | A1 | 10/2006 | Richard | |
| 2007/0157483 | A1 * | 7/2007 | DuMais | A61B 3/111 33/512 |
| 2009/0193675 | A1 * | 8/2009 | Sieber | A41H 1/02 33/759 |
| 2013/0192071 | A1 * | 8/2013 | Esposito | A61B 5/1036 33/6 |
| 2014/0373374 | A1 * | 12/2014 | Znamenskiy | A61B 5/1077 33/512 |
| 2015/0007439 | A1 * | 1/2015 | Todd | A61B 5/1075 33/512 |

OTHER PUBLICATIONS

Anonymous: "Mirage Quattro Mask Fitting Template", ResMed, Feb. 3, 2012, XP002698828, Retrieved from the Internet: URL:http://www.resmed.com/us/assets/documents/service_supportmask_fitting_templates/61858-mirage-quattro-fitting-template.pdf.

"Comfort Gel(TM) and Comfort Select(TM) Best Practice Guide for Sizing & Fitting", 2007 Respironics Inc. www.comfortseries.respironics.com.

"EasyFit(TM) Interfaces Sizing Template", 2009 DeVilbiss Healthcare, www.DevilbissHeathcare.com.

"FitLife Patient and Clinician Fitting Guide", 2009 Koninklijke Philips Electronics N.V., www.philips.com/respironics.

ComfortClassic Nasal Mask Sizing Gauge, Respironics (2007) http://www.medical.philips.com/pwc_hc/au_en/homehealth/sleep/comfortclassic/pdf/GaugeComfortClassicSM.pdf.

* cited by examiner

PATIENT INTERFACE SIZING GAUGE

CROSS-REFERENCE TO RELATED APPLICATIONS

This patent application claims the priority benefit under 35 U.S.C. §371 of international patent application No. PCT/IB2013/050824, filed Jan. 31, 2013, which claims the priority benefit under 35 U.S.C. §119(e) of U.S. Provisional Application No. 61/593,193 filed on Feb. 6, 2012, the contents of which are herein incorporated by reference.

BACKGROUND OF THE INVENTION

1. Field of the Invention

The present invention pertains to patient interfaces for delivering a flow of breathing gas to a patient and, more particular, to an improved sizing gauge that facilitates selection of a patient interface that is sized appropriately for the patient.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a respiratory patient interface device including a patient interface that is typically secured on the face of a patient by a headgear assembly. The patient interface may be, without limitation, a nasal mask that covers the patient's nose, a nasal cushion having nasal prongs that are received within the patient's nares, a nasal/oral mask that covers the nose and mouth, or full face mask that covers the patient's face. It is known to maintain such devices on the face of a wearer by a headgear having one or more straps adapted to fit over/around the patient's head. Because such respiratory patient interface devices are typically worn for an extended period of time, it is important for the headgear to maintain the patient interface in a desired position while doing so in a manner that is comfortable to the patient.

While many mask apparatuses have been generally been effective for their intended purposes, they have not been without limitation. For instance, nasal masks, nasal/oral masks, full face masks, and other types of patient interfaces typically are manufactured in a limited number of sizes and shapes that are intended to fit nearly all patients. However, due to the great variability in the facial geometry of the various patients who need a patient interface, difficulty has been encountered in selecting the patient interface that is sized most appropriately for any given patient.

SUMMARY OF THE INVENTION

In certain embodiments, the general nature of the invention can be stated as including a sizing gauge that is structured to be used with a patient and that is structured to enable an identification of a particular patient interface from among a plurality of patient interfaces that is most appropriately sized for the patient. The sizing gauge can be generally stated as including a support portion and a sizing portion. The sizing portion can be generally stated as including a first gauge element and a plurality of second gauge elements. The first gauge element is disposed on the support portion and is structured to be positioned at a first location on the patient's face. The plurality of second gauge elements are disposed on the support portion and are situated at locations spaced from the first gauge element. The distance between the first gauge element and each second gauge element is representative of a size in one direction of each of at least some of the plurality of patient interfaces. At least one of the plurality of second gauge elements comprises a tactile feature. At least one of the plurality of second gauge elements is structured to be situated at or adjacent a second location on the patient's face to indicate a size in the one direction of the particular patient interface.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
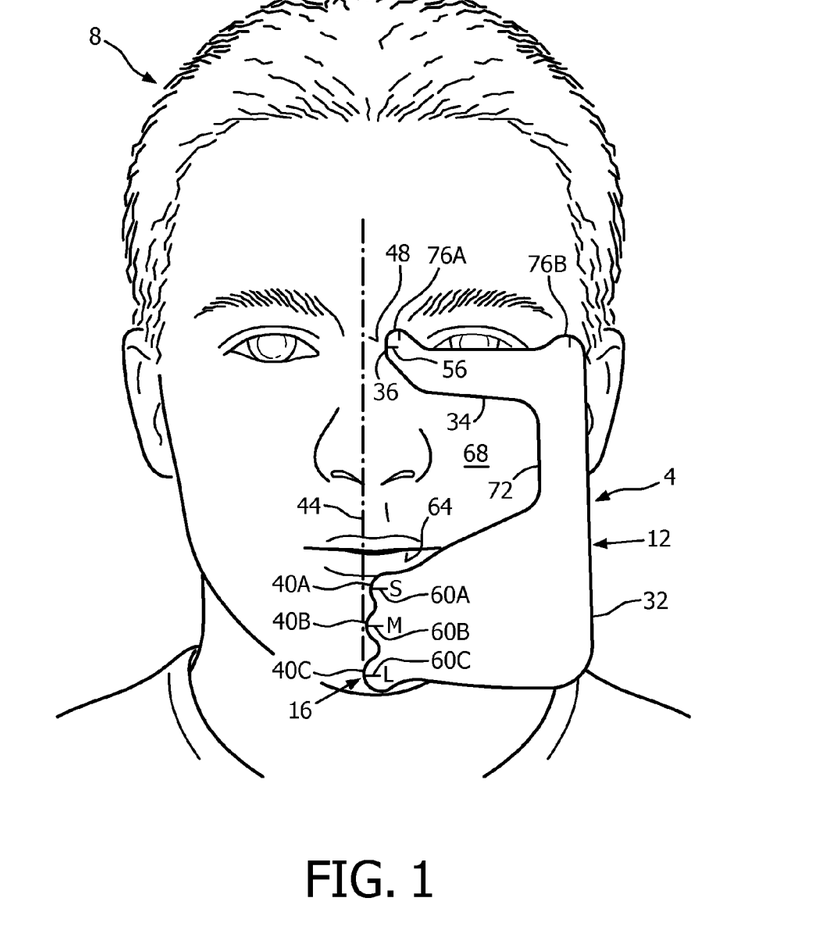
FIG. 1 is a front elevational view of an improved sizing gauge in accordance with the disclosed and claimed concept situated on a patient.

An improved sizing gauge 4 is depicted in FIG. 1 as being situated on the face of a patient 8. Sizing gauge 4 is advantageously configured to enable patient 8, with or without the assistance of a medical professional, to identify a patient interface from among a plurality of patient interfaces that is most appropriately sized to accommodate the specific facial geometry of patient 8.

With brief reference to FIGS. 2A-2F, a plurality of patient interfaces 20A, 20B, 20C, 20D, 20E, and 20F are demonstrated in a schematic fashion to depict the relative abilities of patient interfaces 20A-F to accommodate the varying facial geometries of various patients. While patient interfaces 20A-F and, more particularly, the triangular shape than can said to generally describe the limits of accommodation of the facial geometry of the various patient interfaces 20A-20F, are suggested herein as being nasal/oral patient interfaces, it is understood that patient interfaces 20A-F could alternatively refer to nasal patient interfaces, full face patient interfaces, and the like without limitation.

Figure 2A:
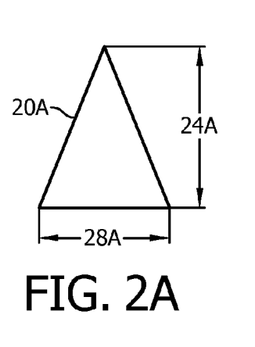
FIGS. 2A-2F depict in a schematic fashion a plurality of patient interfaces and their relative shapes that enable them to accommodate various facial geometries of various patients.
Figure 2B:
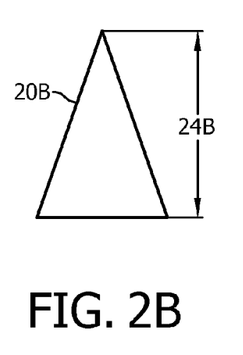
Figure 2C:
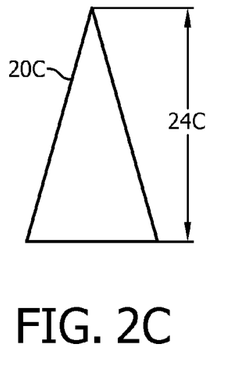

As can be understood from FIGS. 2A-2C, patient interfaces 20A-C each are of a height 24A, 24B, and 24C, respectively. Patient interface 20A also is of a width 28A. While patient interfaces 20A-C are of three varying heights 24A-C, each are of the same width as patient interface 20A, i.e., the same width as is indicated at the numeral 28A. FIGS 2A-C thus illustrate that various patient interfaces, such as patient interfaces 20A-C, can have a size (such as its height) that can vary in one direction.

Figure 2D:
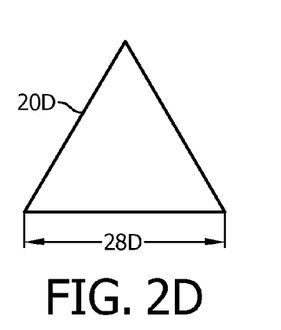
Figure 2E:
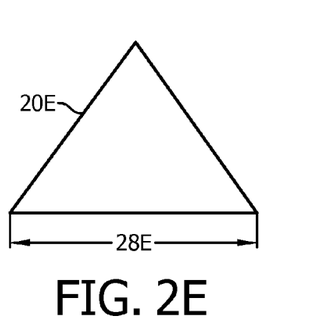
Figure 2F:
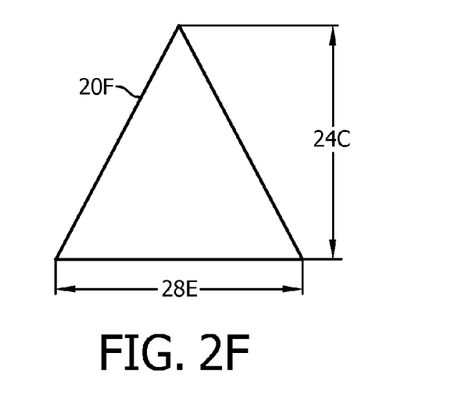

FIGS. 2A, 2D, and 2E are intended to demonstrate that various patient interfaces (such as patient interfaces 20A, 20D, and 20E) can have another size (such as its width) that can vary in a different direction. That is, patient interfaces 20A, 20D, and 20E each have a width indicated at the numerals 28A, 28D, and 28E that are different than one another. However, patient interfaces 20A, 20D, and 20E each have the same height, i.e., the height indicated at 24A as is indicated in FIG. 2A.

Various combinations of heights 24A, 24B, and 24C and widths 28A, 28D, and 28E are possible, and the exemplary patient interface 20F indicates in an how a patient interface can have both the relatively largest height, i.e., 24C, and also have the relatively greatest width, i.e., 28E. It should be apparent that numerous other combinations of sizes are possible than those exemplary combinations of sizes illustrated generally in FIGS. 2A-F. Moreover, it is reiterated that the triangular shapes presented in FIGS. 2A-F are intended merely to illustrate the relative abilities of various patient interfaces 20A-F, and other patient interfaces not expressly depicted herein, to accommodate the varying facial geometries of various patients and the need, therefore, to identify which patient interface from a plurality of patient interfaces is sized most appropriately for any given patient. As will be set forth in greater detail below, sizing gauge 4 advantageously facilitates the selection of a patient interface that is appropriately sized for patient 8.

Again referring to FIG. 1, it can be seen that sizing gauge 4 can be said to include a support portion 12 and a sizing portion 16, with sizing portion 16 being disposed on support portion 12. Support portion 12 can be said to include a base portion 32 and an extension portion 34 that extends from base portion 32.

Sizing portion 16 can be said to include a first gauge element 36 disposed on extension portion 34 and a plurality of second gauge elements 40A, 40B, and 40C disposed on base portion 32. Second gauge elements 40A-C are each spaced along a first direction 44 from first gauge element 36, with second gauge elements 40A, 40B, and 40C each being spaced different distances from first gauge element 36.

In order to determine a height of an appropriately sized patient interface, which would be a dimension oriented parallel with first direction 44, first gauge element 36 is received alongside a bridge 48 of the nose of patient 8. One or more of second gauge elements 40A-C can then be received on patient 8 in another location which, in the exemplary embodiment depicted herein, is in the vicinity of a lower lip 64 of patient 8.

As can be understood from FIG. 1, first gauge element 36 and second gauge elements 40A-C are in the form of rounded protrusions that extend in a direction generally away from support portion 12 in a direction generally perpendicular to first direction 44. The rounded shape of each protrusion serves as a tactile feature that is detectable in a tactile fashion by patient 8 or by a medical professional. Such tactile features facilitate sizing of the appropriate patient interface by enabling patient 8 or the medical professional to rapidly determine the size along first direction 44 that is appropriate to patient 8.

Further in this regard, the apex of each second gauge element 40A-C is employed to indicate the height, i.e., one of heights 24A, 24B, and 24C which correspond with second gauge elements 40A, 40B, and 40C, respectively, and by way of example, that is most appropriate for patient 8. In order to avoid confusion, second gauge elements 40A-C may additionally include a visual indicium 60A, 60B, and 60C at the apex thereof in order to make clear the location on second gauge elements 40A-C that is to be used in determining the appropriate height of the patient interface that is most appropriately sized for patient 8.

The appropriate height for the properly sized patient interface that can be said to be appropriately sized for patient 8 is represented by the second gauge elements 40A, 40B, or 40C that is situated inferior to, i.e., below, lower lip 64 while being closest thereto. In the example of FIG. 1, the apex of second gauge element 40A, as is indicated with indicium 60A, is disposed very slightly inferior to lower lip 64, and can even be said to be situated over a meaningful portion of the soft tissue of lower lip 64. Such a position would probably be undesirable as the location of the lower edge of a patient interface since the force applied to the patient over such soft tissue likely would be undesirable. Thus second gauge element 40B, which correspond with height 28B, is the most appropriate height for the patient interface that will be provided for patient 8.

It is noted that first gauge element 36 includes its own indicium 56 at the apex thereof. Such indicium 56 is optional and may be employed to facilitate aligning the apex of first gauge element 36 with bridge 48 of the nose of patient 8.

It can be seen from FIG. 1 that sizing gauge 4 can be laid across the face of patient 8 and does not obstruct the vision of patient 8. As such, patient 8 can watch in the mirror while individually performing the sizing operations mentioned herein, which facilitates rapid identification of the most appropriately sized patient interface that is appropriate for patient 8.

As can be further understood from FIG. 1, sizing portion 16 additionally can be said to include an indentation 68 that is formed in support portion 12 and which has an indentation edge 72 adjacent indentation 68. As will be set forth in greater detail below, indentation 68 and indentation edge 72 enable an assessment of whether the nose of patient 8 fits within the size limits of the various patient interfaces, i.e., patient interfaces 20A-F and others not expressly depicted herein, that are represented by sizing gauge 4.

Sizing portion 16 can further be said to include a pair of third gauge elements 76A and 76B that are situated on support portion 12. As will be set forth in greater detail below, the pair of third gauge elements 76A-B facilitate the determination of another size of the patient interface that is most appropriately sized for patient 8.

Figure 3:
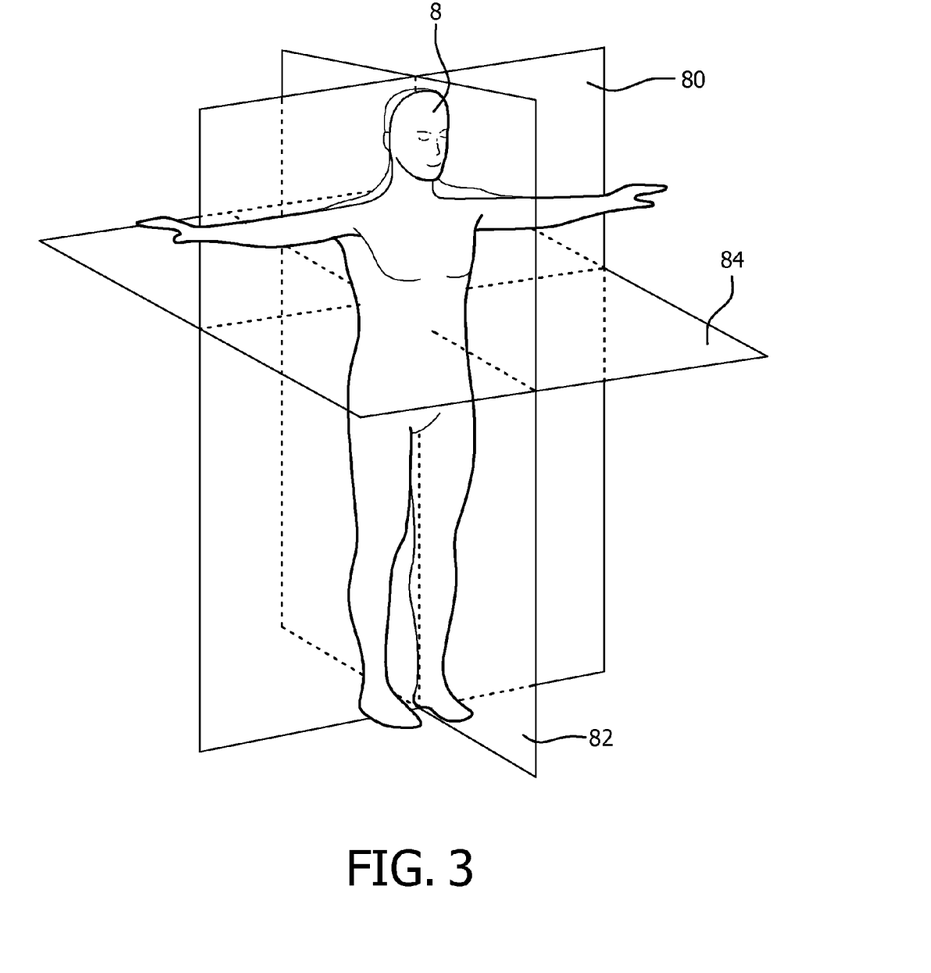
FIG. 3 is a schematic depiction of the patient and the various planes of the body.

As can be understood from FIG. 3, the human body and, in particular, patient 8, can be said to have a plurality of imaginary planes extending therethrough which enable the description of relative positioning and the like. A coronal plane 80 can be said to separate the front of patient 8 from the rear of patient 8. A sagittal plane 82 can be said to separate the right of patient 8 from the left of patient 8. A transverse plane 84 can be said to separate the upper half of patient 8 from the lower half of patient 8.

When sizing gauge 4 is situated on patient 8 in order to assess in first direction 44 the appropriate height of a patient interface for patient 8, sizing gauge 4 is typically oriented substantially parallel with coronal plane 80. That is, sizing gauge 4 is formed from a sheet of material such as cardboard, paper, plastic, etc., and can be said to be of a generally planar configuration. When sizing gauge 4 is situated on patient 8 as is indicated generally in FIG. 1, the plane of sizing gauge 4 will be oriented generally parallel with coronal plane 82. It is understood, however, that depending upon the specific facial geometry of patient 8, sizing gauge 4 may be less than completely parallel with coronal plane 80, although this is acceptable since the distance between first gauge element 36 and one of second gauge elements 40A-C is generally understood to be a distance between two points, which can be assessed regardless of its parallel or non-parallel arrangement with coronal plane 80.

Figure 4:
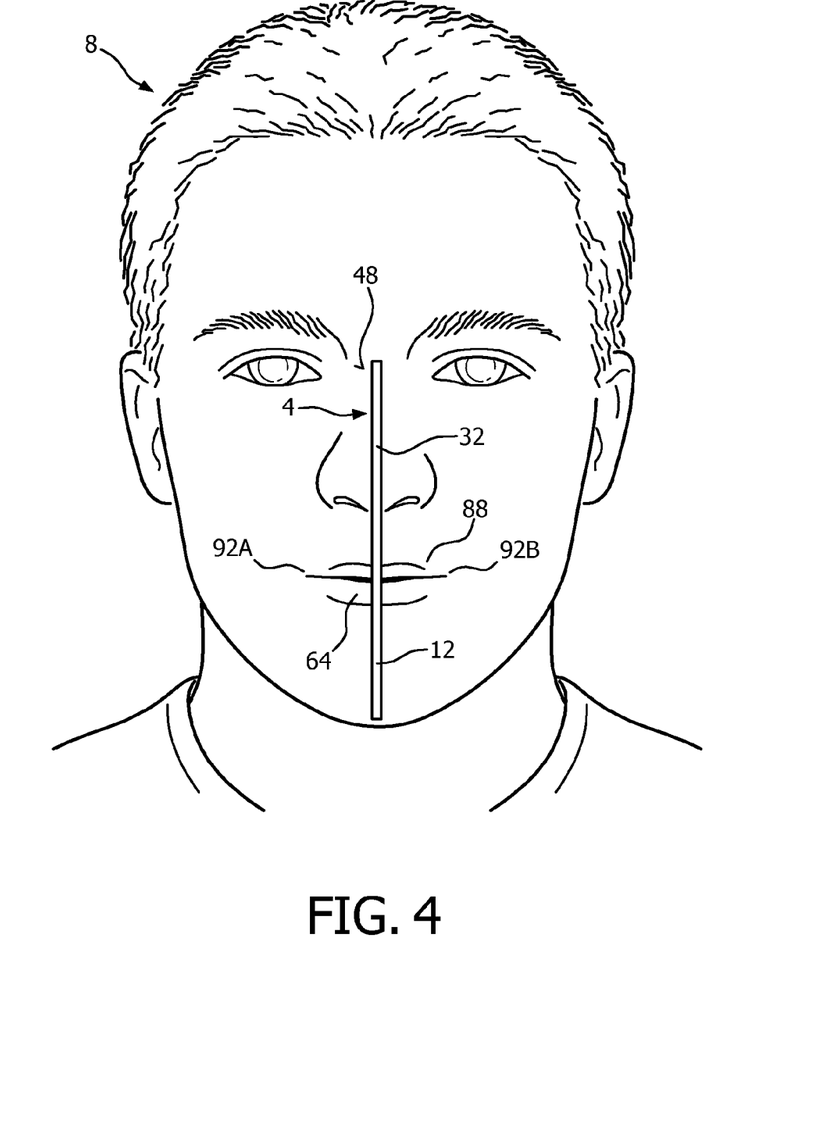
FIG. 4 is another depiction of the sizing gauge positioned on the patient in a different orientation than in FIG. 1.

Further regarding the planar nature of sizing gauge 4, it can be seen from FIG. 4 that sizing gauge 4 is receivable against the face of patient 8 in a different orientation than that depicted generally in FIG. 1. In FIG. 4, support portion 12 is extending away from patient 8 and out of the plane of the page of FIG. 4. A side view of such orientation of sizing gauge 4 is depicted generally in FIG. 5. As can be understood from FIG. 4, however, sizing gauge 4 is of a generally planar configuration, and it can also be seen that the various elements of sizing portion 16, i.e., first gauge element 36, second gauge elements 40A-C, third gauge elements 76A-B, and indentation edge 72 are all substantially coplanar with support portion 12.

Figure 5:
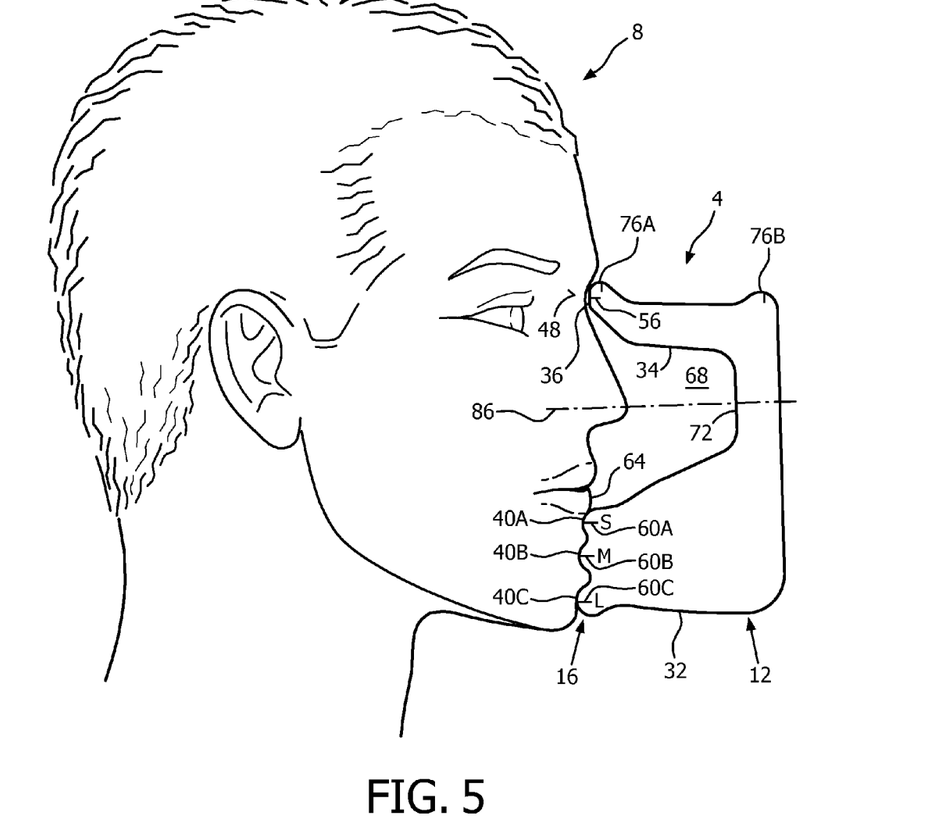
FIG. 5 depicts the sizing gauge in the same orientation as in FIG. 4, except showing the patient in a side profile view.

As can be understood from FIG. 5, the nose of patient 8 is received in indentation 68 and, in the example depicted generally in FIG. 5, is spaced from indentation edge 72. In accordance with the disclosed and claimed concept, indentation edge 72, or at least a portion thereof, can be said to represent the limit by which the nose of patient 8 can be accommodated along a second direction 86 by one or more of patient interfaces 20A-F. That is, sizing gauge 4 is received against the face of patient 8 such that first gauge element 36 is received atop bridge 48 of the nose of patient 8, and second gauge elements 40A-C are received generally against the mouth and/or chin region of patient 8. Sizing gauge 4 is oriented substantially perpendicular to coronal plane 80 in such orientation and thus can also be said to be oriented substantially parallel with sagittal plane 82 in such orientation. As long as the nose does not contact indentation edge 72, the nose will be accommodated in second direction 86 by one or more of patient interfaces 20A-F or another patient interface represented by sizing gauge 4. However, if the nose engages indentation edge 72, it may be necessary to build a custom-configured patient interface for patient 8.

Figure 6:
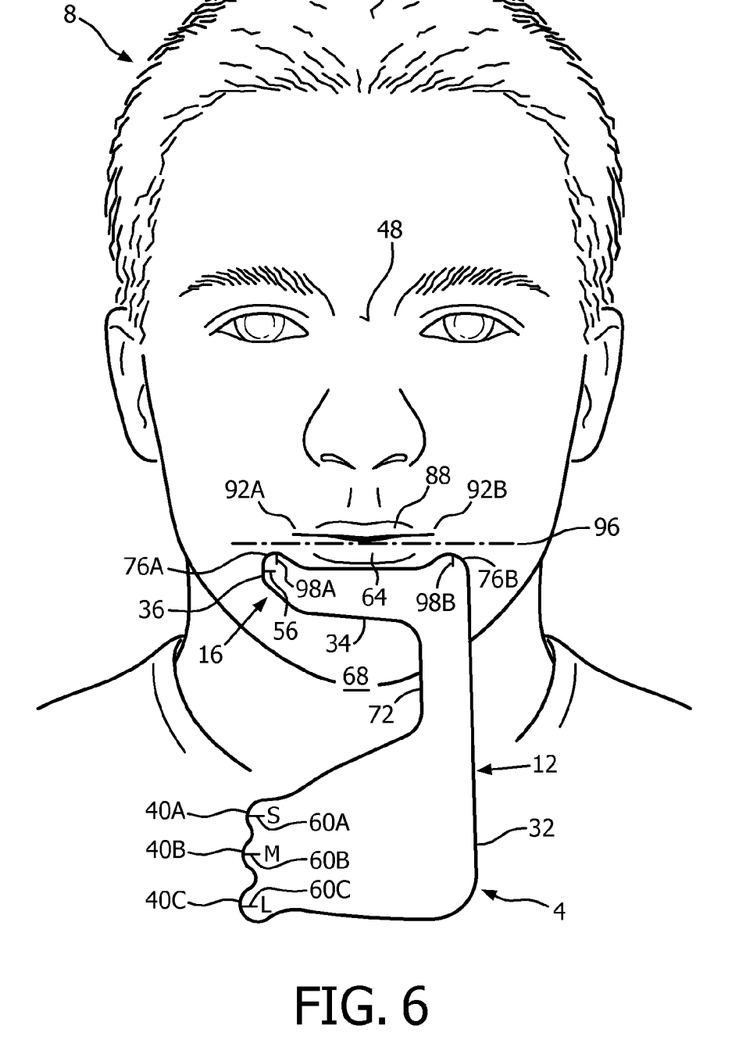
FIG. 6 is a depiction of the sizing gauge in a third orientation on the patient's face.

FIG. 6 depicts sizing gauge 4 arranged on the face of patient 8 in another orientation different than those depicted generally in FIGS. 1 and 5. In particular, the pair of third gauge elements 76A-B are positioned to be in the vicinity of a mouth 88 of patient 8 in order to determine the appropriate sizing of a patient interface along a third direction 96 that is transverse, i.e., perpendicular, to first direction 44. In this regard, it is noted that second direction 86 is perpendicular to first and third directions 44 and 96, thus making first, second, and third directions 44, 86, and 96 mutually orthogonal. In this regard, therefore, it can be understood that sizing gauge 4 assesses the facial geometry of patient 8 in three orthogonal dimensions, while still being of a relatively thin, planar configuration.

Further regarding FIG. 6, it can be seen that third gauge elements 76A and 76B are situated at mouth 88 to determine whether a pair of opposite edges 92A and 92B of mouth 88 are situated between (i.e., inboard of) third gauge elements 76A and B, or whether they are situated beyond (i.e., outboard of) third gauge elements 76A-B. More particularly, the apex of each third gauge element 76A and 76B is used to determine whether mouth 88 is larger along third direction 96 than the distance between the pair of third gauge elements 76A-B, in which case a "large" width patient interface will be required for patient 8, or whether the mouth is of an equal or smaller width than the distance between the pair of third gauge elements 76A and 76B, which would suggest a "medium" or "small" width of a patient interface along third direction 96B.

In this regard, it can be understood that third gauge elements 76A and 76B and, more particularly, the distance therebetween, is in the nature of a threshold distance. That is, a mouth larger than the distance between third gauge elements 76A-B indicates a given size (or larger) of a patient interface, whereas a mouth that is the same size or smaller than the distance between third gauge elements 76A-B indicates another size (or smaller) of a patient interface.

Third gauge elements 76A-B are rounded protrusions, and each have an indicium 98A and 98B, respectively, marked at the apex thereof in order to more precisely define the size threshold represented by the pair of third gauge elements 76A-B.

It should be understood that third gauge elements 76A and B can be positioned elsewhere on sizing gauge 4 without departing from the present concept. Moreover, it is understood that the various arrangements of the components depicted herein is intended to be merely exemplary, and it is expressly noted that they can be of other arrangements than expressly depicted herein without departing from the present concept.

It thus can be understood that sizing gauge 4 enables patient 8, with or without the assistance of a medical professional, to establish the various sizes in three mutually perpendicular directions of a patient interface that will be most appropriately sized for patient 8 based upon the particular facial geometry of patient 8. In this regard, it is noted that specific sizes need not necessarily be established by sizing guide 4 as is apparent from indentation edge 72, which establishes a limit of accommodation of one or more patient interfaces, and by third gauge element 76A-B which establish a size threshold between at least one size and at least one other size. Further variations will be apparent to those having ordinary skill in the relevant art.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A sizing gauge that is structured to be used with a patient and that is structured to enable an identification of a particular patient interface from among a plurality of patient interfaces that is most appropriately sized for the patient, the sizing gauge comprising:
    a support portion;
    a sizing portion comprising:
        a first gauge element,
        a plurality of second gauge elements, wherein the first gauge element is disposed on the support portion and structured to be positioned at a first location on the patient's face, and the plurality of second gauge elements being disposed on the support portion and situated at locations spaced from the first gauge element, the distance between the first gauge element and each second gauge element being representative of a size in one direction that corresponds with a direction generally parallel with the coronal plane of the patient of each of at least some of the plurality of patient interfaces, at least one of the plurality of second gauge elements comprising a tactile feature, at least one of the plurality of second gauge elements being structured to be situated at or adjacent a second location on the patient's face to indicate a size in the one direction of the particular patient interface, and
        an indentation formed in the support portion and situated between the first gauge element and at least one of the plurality of second gauge elements, the support portion having an indentation edge adjacent the indentation, at least a portion of the indentation edge being representative of a limit of the extent to which at least one patient interface from among the plurality of patient interfaces can accommodate the patient in another direction that corresponds with a direction generally parallel with the sagittal plane of the patient.

2. The sizing gauge of claim 1, wherein the sizing gauge is formed from a generally planar sheet of material, and wherein the plurality of second gauge elements are a series of protrusions that protrude from the support portion and are generally coplanar with the support portion.

3. The sizing gauge of claim 1, wherein the sizing gauge is structured to be oriented generally parallel with the coronal plane of the patient when the first gauge element is positioned at the first location on the patient's face and the at least one of the plurality of second gauge elements is situated at or adjacent the second location on the patient's face.

4. The sizing gauge of claim 3, wherein the sizing gauge is structured to be oriented generally perpendicular to the coronal plane of the patient when a portion of the patient is received in the indentation to assess whether the patient is within the limit.

5. The sizing gauge of claim 4, wherein the first gauge element is structured to be positioned at a third location on the patient's face and wherein at least one of the plurality of second gauge elements is structured to be situated at or adjacent a fourth location on the patient's face when the portion of the patient is received in the indentation to assess whether the patient is within the limit.

6. The sizing gauge of claim 5, wherein the first and third locations are adjacent the bridge of the patient's nose, and wherein second and fourth locations are a position inferior to the lower lip of the patient.

7. The sizing gauge of claim 6, wherein the first location is alongside the bridge of the patient's nose and the third location is atop the bridge of the patient's nose.

8. The sizing gauge of claim 1, wherein the sizing portion further comprises a pair of third gauge elements disposed on the support portion and spaced apart from one another, the distance between the pair of third gauge elements being representative of a size in a further direction transverse to the one direction of each of at least some of the plurality of patient interfaces.

9. The sizing gauge of claim 8, wherein the size in the further direction is a size threshold between one size of at least one of the plurality of patient interfaces and another size of at least one of the plurality of patient interfaces.

10. The sizing gauge of claim 9, wherein the pair of third gauge elements are structured to be situated at the mouth of the patient, and wherein the size in the further direction is of at most a first value if the mouth of the patient fits between the pair of third gauge elements and is of at least a second value if the mouth of the patient does not fit between the pair of third gauge elements.

11. The sizing gauge of claim 9, wherein the sizing gauge is formed from a generally planar sheet of material, and wherein the first gauge element, the plurality of second gauge elements, and the pair of third gauge elements are protrusions that protrude from the support portion and are generally coplanar with the support portion.

12. The sizing gauge of claim 11, wherein at least some of the first gauge element, the plurality of second gauge elements, and the pair of third gauge elements are rounded protrusions that additionally include a visual indicium at the crest thereof.

13. The sizing gauge of claim 8, wherein the pair of third gauge elements are disposed on the first gauge element.

* * * * *